United States Patent [19]

Osugi et al.

[11] Patent Number: 4,806,516

[45] Date of Patent: Feb. 21, 1989

[54] PROCESS FOR PRODUCING FLUIDIZED CATALYST FOR SYNTHESIS OF METHANOL

[75] Inventors: Minoru Osugi; Tadasi Nakamura; Yoriko Obata, all of Niigata, Japan

[73] Assignee: Mitsubishi Gas Chemical Company, Inc., Tokyo, Japan

[21] Appl. No.: 77,641

[22] Filed: Jul. 24, 1987

[30] Foreign Application Priority Data

Jul. 24, 1986 [JP] Japan ................... 61-172870

[51] Int. Cl.$^4$ .................. B01J 21/02; B01J 21/06; B01J 23/06; B01J 23/72
[52] U.S. Cl. ................... 502/202; 502/343; 518/713
[58] Field of Search ............ 502/202, 343, 345; 518/713

[56] References Cited

U.S. PATENT DOCUMENTS

| | | | |
|---|---|---|---|
| 4,279,781 | 7/1981 | Dienes et al. | 502/343 |
| 4,386,017 | 5/1983 | Nakamura et al. | 502/174 X |
| 4,666,945 | 5/1987 | Osugi et al. | 502/343 X |

Primary Examiner—W. J. Shine
Attorney, Agent, or Firm—Wenderoth, Lind & Ponack

[57] ABSTRACT

A process for producing a fluidized catalyst for synthesis of methanol, which comprises molding a composition comprising
  (A) 10 to 55% by weight of a mixture composed of water-insoluble copper, zinc and zirconium compounds convertible respectively to copper, zinc and zirconium oxides under calcination conditions, said mixture optionally containing a boron compound,
  (B) 45 to 90% by weight of water, and
  (C) 0.01 to 1% by weight of ammonia into fine particles, and calcining the fine particles.

9 Claims, No Drawings

PROCESS FOR PRODUCING FLUIDIZED CATALYST FOR SYNTHESIS OF METHANOL

This invention relates to a process for producing a fluidized catalyst for synthesis of methanol which has high activity and excellent attrition resistance.

In the synthesis of methanol by reacting carbon oxide (carbon monoxide and/or carbon dioxide) and hydrogen, a process involving the use of a fluidized bed brings about many advantages such as adaptability to various starting gases, scale up, and energy unit reduction. Copper-zinc-aluminum type catalysts (Japanese Laid-Open Patent Publications Nos. 84142/1985 and 122040/1985) and a copper-zinc-zirconium type catalyst (U. S. Pat. No. 4,666,945 corresponding to Japanese Laid-Open Patent Publication No. 106534/1985), for example, are known as catalysts used in the fluidized bed process. Thee catalysts, however, do not exhibit sufficient activity, and it has still been desired to develop a catalyst having higher activity.

The present inventors have now found that a fluidized catalyst for synthesis of methanol having high activity and excellent attrition resistance can be obtained by including a specific amount of ammonia into a catalyst precursor composition and controlling the water content of the composition in the production of a copper-zinc-zirconium type catalyst.

According to this invention, there is provided a process for producing a fluidized catalyst for synthesis of methanol, which comprises molding a composition comprising (A) 10 to 55% by weight of a mixture composed of water-insoluble copper, zinc and zirconium compounds convertible respectively to copper, zinc and zirconium oxides under calcination conditions, said mixture optionally containing a boron compound, (B) 45 to 90% by weight of water, and (C) 0.01 to 1% by weight of ammonia into fine particles, and calcining the fine particles.

The catalyst provided by the process of this invention may consist essentially of an intimate mixture of three essential components, copper oxide, zinc oxide and zirconium oxide. The proportions of these three components in the catalyst may be as follow:

|  | General range (wt. %) | Preferred range (wt. %) | More preferred range (wt. %) |
|---|---|---|---|
| Copper oxide | 10–67 | 20–55 | 30–45 |
| Zinc oxide | 1.5–47 | 5–40 | 10–30 |
| Zirconium oxide | 30–70 | 40–60 | 45–55 |

The content of the boron compound which may be included in the catalyst as an optional component is generally up to 5% by weight, specifically 0.3 to 5% by weight, preferably 0.5 to 3% by weight. The ratio of copper oxide to zinc oxide in the catalyst composition is not strictly limited and can be changed depending upon the conditions under which a reaction of synthesizing methanol is carried out in the presence of the above catalyst. Usually, it is advantageous that copper oxide and zinc oxide are present in such proportions that the Cu/Zn atomic ratio is from 0.5/1 to 20.0/1, preferably from 0.8/1 to 15.0/1, more preferably from 0.8/1 to 5/1.

In the production of a Cu—Zn—Zr three-component catalyst or a Cu—Zn—Zr—B four-component catalyst having the above composition, the starting uniform mixture composed of water-insoluble copper, zinc and zirconium compounds can be prepared, for example, by various methods to be described below.

(a) A method which comprises adding a suitable precipitating agent to a mixed aqueous solution of water-soluble copper, zinc and zirconium compounds to co-precipitate a mixture of water-insoluble copper, zinc and zirconium compounds.

(b) A method wherein from a mixed aqueous solution of any two of a water-soluble copper compound, a water-soluble zinc compound and a water-soluble zirconium compound, two water-insoluble compounds of the metals of the two soluble compounds are coprecipitated, the remaining water-soluble metal compound is added and dissolved in the coprecipitate-containing slurry and a water-insoluble compound of its metal is precipitated; or a slurry of water-insoluble compound of the metal of the remaining water-soluble metal compound separately precipitated is added to the above slurry containing the coprecipitate; or the above procedure is conducted in a reverse sequence.

(c) A method which comprises precipitating a water-insoluble copper compound, a water-insoluble zinc compound and a water-insoluble zirconium compound separately from an aqueous solution of a water-soluble copper compound, an aqueous solution of a water-soluble zinc compound and an aqueous solution of a water-soluble zirconium compound and mixing them in the form of a precipitate-containing slurry; or separating the precipitates by filtration and then kneading them with one another.

(d) A method wherein in order to form a mixed aqueous slurry of a water-insoluble copper and/or zirconium compound and a water-insoluble zinc compound in the above method (b), zinc oxide or zinc hydroxide is added to a water-insoluble copper and/or zirconium compound precipitated from an aqueous solution of a water-soluble copper and/or zirconium compound to form an aqueous slurry and then carbon dioxide gas is blown into the aqueous slurry to convert zinc oxide or zinc hydroxide to basic zinc carbonate.

The boron compound may be added to the precipitation reaction system in any desired stage in each of the methods (a) to (d) described above.

Water-soluble copper compounds used as starting materials in these methods include water-soluble copper salts usually employed for the preparation of the aforesaid conventional catalysts. Specific examples are cupric nitrate, cupric acetate and cupric oxalate. Those which do not contain elements acting as catalyst poisons such as halogen and sulfur are preferred. Cupric nitrate is especially preferred.

Water-soluble zinc compounds may be any water-soluble zinc salts which are usually employed for the preparation of the aforesaid conventional catalysts. Specific examples include zinc nitrate and zinc acetate. Of these salts, preferred are those not containing elements that become catalyst poisons such as halogen and sulfur. Zinc nitrate is particularly preferred.

Basic zinc carbonate obtained by blowing carbon dioxide gas into a suspension of zinc oxide or zinc hydroxide may likewise be used as the water-insoluble zinc compound. The starting zinc oxide in this case preferably has an average crystal diameter of 200 to 300 Å.

Examples of the water-soluble zirconium compound that can be used in the above methods include organic or inorganic acid salts of zirconium such as zirconium oxynitrate and zirconium acetate. Preferably, these salts neither contain elements that become catalyst poisons, such as halogen and sulfur. Zirconium oxynitrate is especially preferred.

In order to form a water-insoluble zirconium compound, it is also possible to use zirconium compounds which are soluble in suitable solvents and can form a precipitate under suitable conditions, for example, zirconium alkoxides such as zirconium tetrabutoxide. The zirconium alkoxide can dissolve in a solvent such as an alcohol and upon addition of water, form a water-insoluble zirconium compound.

In the aforesaid methods, examples of the precipitating agent that can be used in the (co)precipitation of the water-insoluble copper and/or zinc and/or zirconium compound(s) from the aqueous solution(s) of the water-soluble copper and/or zinc and/or zirconium compound(s) may be water-soluble alkaline substances such as ammonia; alkali carbonates such as sodium carbonate, potassium carbonate, lithium carbonate and ammonium carbonate, alkali bicarbonates such as sodium bicarbonate, potassium bicarbonate and ammonium bicarbonate; and alkali metal hydroxides such as sodium hydroxide, potassium hydroxide and lithium hydroxide. The precipitating agent can usually be employed in an amount of at least 0.8 equivalent, preferably 1 to 2 equivalents, more preferably 1.0 to 1.3 equivalents, per equivalent of the water-soluble metal compound to be subjected to precipitation.

The reaction of forming the precipitate of the water-insoluble metal compound(s) from the aqueous solution(s) of the water-soluble metal compound(s) can be performed according to methods known per se, for example the methods described in U.S. Pat. Nos. 3,971,735 and 4,305,842 and UK Patent Application No. 2064352A. The reaction may be carried out, for example, at room temperature or if required, at an elevated temperature of up to about 90° C. Under these conditions, the reaction can proceed smoothly and be terminated almost quantitatively within several minutes to several tens of minutes.

The concentration each of the water-soluble metal compounds in the aqueous solution in the precipitation reaction is not critical and can be varied broadly depending upon the types of the compounds. Generally it is 0.05 mole/liter to the limit of dissolution of the compound(s), preferably 0.1 to 5 moles/liter.

The uniform mixture so formed of the water-insoluble copper, zinc and zirconium compounds is filtered, washed if necessary and then formed into a slurry in a concentration suitable for pulverization. The slurry is molded into fine particles by spray-drying or dropping it onto an oil in a usual manner.

The concentration of the slurry varies with the composition of the uniform mixture, pulverizing method, etc. Generally, it is convenient to set the concentration such that the solids content is 5 to 40% by weight, preferably 10 to 30% by weight, based on the aqueous medium.

To prepare the Cu—Zn—Zr—B four-component catalyst containing the additional component (boron compound) as well as the three essential components (copper oxide, zinc oxide and zirconium oxide), the boron compound can be added to an aqueous solution containing the above mixture of copper, zinc and zirconium compounds at any desired stage during formation of the uniform mixture of water-insoluble copper, zinc, and zirconium compounds.

Examples of the boron compound to be added optionally are boric acid, borax and ammonium borate. Boric acid is especially preferred.

The water-insoluble copper, zinc and zirconium compounds which are formed as stated above can be converted substantially to copper, zinc and zirconium oxides under calcination conditions to be described. Specific examples of such compounds are basic copper carbonate, copper hydroxide, copper carbonate, basic zinc carbonate, zinc hydroxide, zinc carbonate, basic zirconium carbonate, zirconium hydroxide and zirconium carbonate.

These water-insoluble copper, zinc, zirconium and boron compounds are included in the aforesaid mixture in amounts corresponding to the desired contents of copper, zinc and zirconium oxide and boron compound in the final catalyst product.

The ammonia component is introduced into the mixture prepared as above of water-insoluble copper, zinc and zirconium compounds and optionally the boron compound. Sources of the ammonia component may include aqueous ammonia and water-soluble ammonium salts such as ammonium bicarbonate and ammonium carbonate. Aqueous ammonia is preferred. The content of the ammonia source may be 0.01 to 1% by weight, preferably 0.05 to 0.8% by weight, more preferably 0.05 to 0.5% by weight, calculated as ammonia ($NH_3$), based on the composition immediately before submission to the particle-forming step.

It should be understood that the term "ammonia", as used in the present specification and the appended claims, is used to denote aqueous ammonia and the above-exemplified water-soluble ammonium salts generically, and its content is expressed as the calculated amount of ammonia ($NH_3$).

The addition of ammonia can prevent the reduction with time of the catalytic activity which is most important to industrial catalysts.

It is important that the water content of the composition immediately before submission to the pulverization step (to be sometimes referred to as the "catalyst precursor composition") should be adjusted to 45 to 90% by weight, preferably 60 to 85% by weight, more preferably 70 to 80% by weight, based on the catalyst precursor composition by adding water as required to the aforesaid mixture. If the water content of the catalyst precursor composition is less than 45% by weight, the effect of adding ammonia stated above cannot be fully exhibited, and the attrition resistance of the resulting catalyst cannot be fully increased. If the water content exceeds 90% by weight, the attrition resistance of the catalyst is impaired, and a large quantity of thermal energy is required at the time of drying. This is not economical.

The catalyst precursor composition of the above mixture composed of water-insoluble copper, zinc and zirconium compounds and optionally containing a boron compound may have a solids content of 10 to 55% by weight, preferably 15 to 40% by weight, more preferably 20 to 30% by weight.

The catalyst precursor composition is then molded into fine particles and dried. The molding and drying may be performed as separate steps. Generally, however, it is convenient to perform them by using a particle-forming method in which molding into fine particles and drying of the fine particles can be carried out nearly simultaneously. Spray-drying and dropping into an oil may be cited as examples of such a particle-forming method. Spray-drying is especially preferred.

The catalyst precursor particles so prepared are then calcined. The calcination can be carried out by a method known per se. For example, the catalyst precursor particles are heated at a temperature of at least 280° C., preferably 300 to 500° C., for about 0.3 to 3 hours in an atmosphere of air, a combustion gas, etc. in a calcination furnace such as an electrical furnace or a gas calcination furnace.

The powdery catalyst so prepared may have a particle diameter of 5 to 3,000 microns which is the same as catalysts used in an ordinary fluidized catalyst bed reactor. When the catalyst is used in a gas-phase fluidized catalyst bed reaction, it is frequently impossible to obtain a good fluidized condition if the catalyst contains a large amount of particles with a particle diameter of more than 500 microns. Generally preferred are nearly spherical particles having a particle diameter of 20 to 200 microns with a suitable particle size distribution.

The catalyst prepared by this invention, after it is subjected to an activation treatment such as reduction with hydrogen as is usually the case, can be used as a fluidized bed catalyst for various reactions, for example, a reaction of synthesizing methanol from a gaseous mixture of carbon monoxide and/or carbon dioxide and hydrogen, a carbon monoxide conversion reaction, a hydrogenation reaction, and a methanol decomposition reaction.

The activation treatment of the catalyst in the invention may be carried out in a customary manner, for example, by reducing it with a hydrogen-containing gas. For example, it is carried out in a reducing atmosphere such as a starting gas for synthesis of methanol by raising the temperature of the catalyst gradually from about 140° C. to avoid abrupt generation of heat, and finally maintaining the catalyst at 240° C. for 3 hours.

The activated catalyst is particularly suitable for catalyzing synthesis of methanol using a fluidized catalyst bed from a gaseous mixture of carbon monoxide and/or carbon dioxide and hydrogen. Synthesis of methanol with the catalyst prepared by this invention can be carried out by a method known per se, for example by the method described in U. S. Patent No. 4,386,017. For example, the synthesis reaction can be performed by feeding the aforesaid gaseous mixture into a reaction zone having a fluidized catalyst bed at a pressure of 20 to 300 kg/cm$^2$-G, preferably 30 to 200 kg/cm$^2$-G, a temperature of 150 to 350° C., preferably 200 to 300° C., and a space velocity of 1,000 to 80,000 hr$^{-1}$. In particular, when the catalyst is used in a gas-phase fluidized bed method, the superficial velocity of the gas in a column should also be considered in order to effect sufficient fluidization of the catalyst particles.

The catalyst provided by the present invention has high catalytic activity on synthesis of methanol and excellent attrition resistance, and can be advantageously employed in both (a) a method of methanol synthesis using a gas-liquid-solid three-phase fluidized bed wherein methanol is synthesized by dispersing a solid catalyst in an inert liquid medium such as a hydrocarbon oil and introducing carbon monoxide and/or carbon dioxide and hydrogen gas into the dispersion, and (b) a method of methanol synthesis using a gas-phase fluidized bed wherein methanol is synthesized while fluidizing the solid catalyst powder by blowing carbon monoxide and/or carbon dioxide and hydrogen gas into a bed packed with the solid catalyst powder.

The following examples illustrate the present invention more specifically.

EXAMPLE 1

Copper nitrate trihydrate (12.45 kg) was dissolved in 77 liters of deionized water, and the solution was maintained at 40° C. Then, 9.15 kg of ammonium bicarbonate was dissolved in 92 liters of deionized water, and the solution was maintained at 40° C. With stirring, the above aqueous copper nitrate solution was added to the ammonium bicarbonate solution to prepare a copper slurry. Separately, 1.4 kg of zinc oxide obtained by thermally decomposing basic zinc carbonate at 300° C. was added to 20 liters of deionized water, and the mixture was stirred for 30 minutes to prepare a slurry of zinc oxide. The resulting slurry was added to the above copper slurry. Carbon dioxide gas was blown into the mixture at a flow rate of 320 liters/hr. At this time, the slurry was maintained at 40° C. and after the lapse of 40 minutes, heated to 70° C. and aged at this temperature for 30 minutes. It was then cooled to 40° C. and maintained at this temperature. To the resulting Cu—Zn slurry were added a solution (40° C.) of 22 kg of an aqueous solution of zirconium oxynitrate (containing 25% of $ZrO_2$) in 47 liters of deionized water and a solution (40° C.) of 7.92 kg of ammonium bicarbonate in 100 liters of deionized water, and the mixture was maintained at the above temperature for 30 minutes. It was then filtered and washed to obtain a cake. When the cake was dried at about 100° C., it had an average water content of 68%. The above hydrous cake was again well disintegrated and ground by a mixer, and its ammonia concentration was examined by an ion meter and found to be 0.008% by weight. A slurry (solids concentration 23% by weight) for spray-drying was prepared in a Henschel mixer using 10 kg (dry weight) of the above cake and 0.05% by weight, as ammonia, of aqueous ammonia as an ammonia source, and then spray-dried to form a powder composed of spherical particles. The powder was fluidized in an air current and calcined at 380° C. for 2 hours to obtain a calcined product having an average particle diameter of 60 microns (catalyst A).

EXAMPLE 2

The cake obtained in Example 1 was dried at 50° C. under reduced pressure to obtain a cake having an average water content of 50%. A slurry (solids concentration 24%) was prepared a in Example 1 using 7 kg of the cake and 0.1% by weight, as ammonia, of aqueous ammonia as an ammonia source, and then spray-dried and treated as in Example 1 to obtain a calcined product having an average particle diameter of 65 microns (catalyst B).

EXAMPLE 3

Copper nitrate trihydrate (2.28 kg) and 0.19 kg of boric acid were dissolved in 17.5 liters of deionized water, and the solution was maintained at 40° C. Then, 1.13 kg of soda ash was dissolved in 14 liters of deionized water and the solution was maintained at 40° C. With stirring, the above aqueous copper nitrate solution was added to this solution to prepare a copper slurry.

Separately, 0.38 kg of zinc oxide obtained by thermally decomposing basic zinc carbonate at 300° C. to 4 liters of deionized water to prepare a slurry of zinc oxide. The resulting slurry was added to the copper slurry described above. Carbon dioxide gas was blown into the mixed slurry at a rate of 60 liters/hr. After standing at 40° C. for 40 minutes, the mixture was heated to 70° C., aged at this temperature for 30 minutes, then cooled, filtered and washed to obtain about 3.3 kg (water content 60%) of a cake.

2.2 kg of an aqueous solution of zirconium oxynitrate (containing 25% of $ZrO_2$) was dissolved in 10 liters of deionized water and the mixed solution was maintained at 40° C. Then, 0.79 kg of ammonium bicarbonate was dissolved in 20 liters of deionized water. The solution was maintained at 40° C., and with stirring, the above aqueous zirconium oxynitrate solution was added to this solution. The mixture was maintained at the above temperature for 30 minutes, and then filtered and washed to obtain about 3.3 kg (water content 80%) of a cake as a source of zirconium oxide. The cake contained 0.07% by weight of ammonia.

A slurry (solids content 20%) for spray drying was prepared in a Henschel mixer using 2 kg of the cake containing copper and zinc, 1.57 kg of of the cake as a source of zirconium oxide, 2 kg of water and 175 g of 25% aqueous ammonia. The slurry contained 0.8% by weight of ammonia. The slurry was spray-dried and treated as in Example 1 to obtain a calcined product having an average particle diameter of 52 microns (catalyst C).

EXAMPLE 4

Copper nitrate trihydrate (2.84 kg), 0.7 kg of zinc nitrate hexahydrate, and 0.22 kg of boric acid were dissolved in 28 liters of deionized water, and the solution was maintained at 40° C. Then, 2.45 kg of ammonium bicarbonate was dissolved in 60 liters of deionized water, and the solution was maintained at 40° C. With stirring, the above aqueous solution containing copper, zinc and boric acid was added to this solution. The mixture was heated to 70° C. over the course of 30 minutes, then cooled and maintained at 40° C. To this Cu—Zn slurry were added with stirring a solution (40° C.) of 6.76 kg of an aqueous solution of zirconium oxynitrate (containing 25% of $ZrO_2$) in 26 liters of deionized water and a solution (40° C.) of 2.44 kg of ammonium bicarbonate in 60 liters of deionized water. The mixture was maintained at the above temperature for 30 minutes and then filtered and washed to obtain a cake having a water content of 70% and an ammonia content of 0.04% by weight. A slurry (solids content 23%) was prepared in a Henschel mixer using 5 kg of the cake and 0.7%, as ammonia, of an aqueous solution of ammonium bicarbonate as an ammonia source, and spray-dried and treated as in Example 1 to obtain a calcined product having an average particle diameter of 57 microns (catalyst D).

COMPARATIVE EXAMPLE 1

A slurry (solids concentration 23%, ammonia content 0.003% by weight) was prepared in a Henschel mixer using the cake obtained in Example 1, and then spray-dried and treated as in Example 1 to obtain a calcined product having an average particle diameter of 60 microns (catalyst E).

COMPARATIVE EXAMPLE 2

The cake used in Example 1 was dried at 50° C. under reduced pressure as in Example 2 to prepare a cake having a water content of 40%. The cake was hard and seen to be in the process of being converted to a xerogel. Water was added to this material to a solids content of 44%, and the mixture was kneaded for 6 hours in a mixing and grinding machine. Water and aqueous ammonia (ammonia 0.1%) were then added so that the solids concentration became 22%. After kneading for two hours further, many hard small particles were observed. When such particles were spray-dried, troubles such as nozzle blockage frequently occurred. The resulting calcined product (catalyst F) was not in a good spherical shape.

TEST EXAMPLES 1-6

Activity test:

One hundred milliliters of each of the catalysts A to F was filled in a stainless steel reactor having an inside diameter of 30 mm and provided at its lower part with a filter made of sintered metal. Nitrogen gas was introduced into the reactor through the filter at the lower part, and the reactor was maintained at 140° C. Then, the nitrogen gas was gradually replaced by hydrogen gas. The temperature was elevated to 240° C., and the catalyst was maintained at this temperature for 3 hours to reduce it.

A synthesis gas composed of 23% of carbon monoxide, 7.2% of carbon dioxide, 1.5% of methane, 1.2% of nitrogen and 67.1% of hydrogen was reacted in the above reactor at a temperature of 260° C., a pressure of 70 kg/cm$^2$ and a space velocity of $2 \times 10^4$ hr$^{-1}$.

To determine the life of the catalyst within a short period of time, the temperature of the catalyst was elevated to 360° C. and synthesis of methanol was carried out for 2 hours. The temperature was lowered to 260° C., and the activity of the catalyst at this time was measured. Furthermore, the temperature was again raised to 360° C., and methanol synthesis was carried out for 8 hours (total 10 hours). Then, the temperature was again lowered to 260° C., and the activity of the catalyst was measured. The activities were expressed by the methanol concentrations in the gas at the outlet of the reactor. The results are shown in Table 1.

TABLE 1

| Test Example | Catalyst designation | Composition before spray-drying | | | | Methanol concentration (mole %) in the gas at the outlet of the reactor (reaction temperature 260° C.) | | |
|---|---|---|---|---|---|---|---|---|
| | | Water content (wt. %) | Ammonia content (wt. %) | Cu/Zn atomic ratio | $ZrO_2$ content (wt. %) | Initial stage | After treatment for 2 hours | After treatment for 10 hours |
| 1 | A | 77 | 0.05 | 3.0 | 50 | 15.12 | 15.00 | 14.57 |
| 2 | B | 76 | 0.10 | 3.0 | 50 | 15.05 | 14.95 | 14.50 |
| 3 | C | 80 | 0.80 | 2.0 | 30 | 17.75 | 16.56 | 14.20 |
| 4 | D | 77 | 0.70 | 5.0 | 60 | 14.80 | 14.21 | 13.85 |
| 5 | E | 77 | 0.003 | 3.0 | 50 | 14.12 | 12.66 | 10.10 |

TABLE 1-continued

| Test Example | Catalyst designation | Composition before spray-drying | | | | Methanol concentration (mole %) in the gas at the outlet of the reactor (reaction temperature 260° C.) | | |
|---|---|---|---|---|---|---|---|---|
| | | Water content (wt. %) | Ammonia content (wt. %) | Cu/Zn atomic ratio | ZrO$_2$ content (wt. %) | Initial stage | After treatment for 2 hours | After treatment for 10 hours |
| 6 | F | 78 | 0.10 | 3.0 | 50 | 13.85 | 12.00 | 10.00 |

TEST EXAMPLES 7-9

Attrition test:

Fifty grams of each of the spherical catalyst powders (calcined) obtained in Examples 1 and 3 and Comparative Example 2 was fluidized in a nitrogen stream and maintained at 140° C. The nitrogen gas was then gradually replaced by hydrogen gas, and over the course of about 5 hours, all the nitrogen gas was replaced by hydrogen gas. The catalyst was then maintained at 240° C. for 3 hours to reduce it.

The reduced catalyst was filled in a thick glass tube having an inside diameter of 270 mm and provided at its lower part with a stainless steel plate having small holes with a diameter of 0.4 mm. A gas exhaust tube provided with a cylindrical filter paper was inserted into the upper part of the glass tube to avoid escape of the catalyst powder out of the glass tube.

Nitrogen was jetted out for 1 hour at a rate of 510 liters/hr from the small holes formed in the stainless steel plate to attrite the catalyst particles. Jetting of nitrogen was then stopped, and air was passed through the glass tube little by little for 15 hours to re-oxidize the catalyst. Nearly all of the catalyst powder was recovered.

The particle size distribution of the catalyst particles was measured by a sonic-type hand sifter (Model SW-20 made by Tsutsui Rikagakukikai K. K.) before and after the above attrition test. The attrition speed was determined in accordance with the following equations.

$$AR(-20) = (A-B)/C \times 100 \ (\%)$$

$$AR(-44) = (D-E)/F \times 100 \ (\%)$$

In the equations:

AR(−20) is the attrition speed (%) determined from variations in the proportion of particles having a particle diameter of less than 20 microns;

AR(−44) is the attrition speed (%) determined from variations in the proportion of particles having a particle diameter of less than 44 microns;

A is the proportion (% by weight) of particles having a particle diameter of less than 20 microns in the re-oxidized catalyst particles recovered after the attrition test;

B is the proportion (% by weight) of particles having a particle diameter of less than 20 microns in the calcined catalyst particles before the attrition test;

C is the proportion (% by weight) of particles having a particle diameter of at least 20 microns in the calcined catalyst particles before the attrition test;

D is the proportion (% by weight) of particles having a particle diameter of less than 44 microns in the re-oxidized catalyst particles recovered after the attrition test;

E is the proportion (% by weight) of particles having a particle diameter of less than 44 microns in the calcined catalyst particles before the attrition test;

F is the proportion (% by weight) of particles having a particle diameter of at least 44 microns in the calcined catalyst particles before the attrition test.

The results are shown in Table 2 together with the results of Referential Examples 1 and 2 in which commercial catalysts were used.

TABLE 2

| Test Example | Catalyst | Attrition speed (wt. %/hr) | |
|---|---|---|---|
| | | AR (−20) | AR (−44) |
| 7 | A | 4.2 | 4.9 |
| 8 | C | 19.6 | 29.8 |
| 9 | F | 60.9 | 80.2 |
| Ref. Ex. 1 | G (*1) | 20.6 | 32.4 |
| Ref. Ex. 2 | H (*2) | 29.1 | 37.7 |

(*1): Silica-alumina catalyst for FCC (L.A made by Shokubai Kasei K.K.).
(*2): Silica-alumina catalyst for FCC (SZ-H) made by Shokubai Kasei K.K.).
Ref. Ex. = Referential Example

What is claimed is:

1. A process for producing a fluidized catalyst for synthesis of methanol, which comprises molding a composition comprising
   (A) 10 to 55% by weight of a mixture composed of water-insoluble copper, zinc and zirconium compounds convertible respectively to copper, zinc and zirconium oxides under calcination conditions, said mixture optionally containing a boron compound,
   (B) 45 to 90% by weight of water, and
   (C) 0.01 to 1% by weight of ammonia into fine particles, and calcining the fine particles.

2. The process of claim 1 wherein the composition contains 15 to 40% by weight of the mixture (A).

3. The process of claim 1 wherein the composition contains 60 to 85% by weight of water (B).

4. The process of claim 1 wherein the composition contains 0.05 to 0.8% by weight of ammonia (C).

5. The process of claim 1 wherein the molding of the composition into fine particles is carried out by spray-drying.

6. The process of claim 1 wherein the calcination of the fine particles is carried out by heating them at a temperature of 300 to 500° C. in an atmosphere of air.

7. The process of claim 1 wherein the fluidized catalyst is a powdery catalyst composed of a uniform mixture consisting essentially of 10 to 67% by weight of copper oxide, 1.5 to 47% by weight of zinc oxide, 30 to 70% by weight of zirconium oxide and up to 5% by weight of a boron compound.

8. The process of claim 7 wherein the production of copper oxide and zinc oxide are such that the Cu/Zn atomic ratio is from 0.5/1 to 20.0/1.

9. The process of claim 1 wherein the fluidized catalyst is a powdery catalyst having a particle diameter of 20 to 200 microns.

* * * * *